United States Patent [19]

Azuma et al.

[11] Patent Number: 5,049,359
[45] Date of Patent: Sep. 17, 1991

[54] APPARATUS FOR BIOCHEMICAL ANALYSIS

[75] Inventors: Masahi Azuma, Hino; Yasuhiro Satoh, Niiza; Takashi Ishihara, Tachikawa, all of Japan

[73] Assignee: Konishiroku Photo Industry Co., Ltd., Tokyo, Japan

[21] Appl. No.: 489,870

[22] Filed: Mar. 6, 1990

Related U.S. Application Data

[63] Continuation of Ser. No. 186,682, Apr. 21, 1988, abandoned, which is a continuation of Ser. No. 38,446, Apr. 14, 1987, abandoned, which is a continuation of Ser. No. 833,598, Feb. 27, 1986, abandoned.

[30] Foreign Application Priority Data

Feb. 28, 1985 [JP] Japan .................. 60-39875

[51] Int. Cl.$^5$ ............................. G01N 35/00
[52] U.S. Cl. ........................ 422/67; 422/63; 422/64; 436/46; 364/497
[58] Field of Search ..................... 422/63-67; 436/46-48, 50; 364/497

[56] References Cited

U.S. PATENT DOCUMENTS

| | | | |
|---|---|---|---|
| 4,119,407 | 10/1978 | Goldstein et al. | 422/72 X |
| 4,219,529 | 8/1980 | Tersteeg et al. | 422/64 X |
| 4,224,032 | 9/1980 | Glover et al. | 436/46 |
| 4,226,537 | 10/1980 | Colley | 422/101 X |
| 4,272,482 | 6/1981 | Jessop et al. | 422/66 X |
| 4,296,069 | 10/1981 | Smith et al. | 422/64 |
| 4,296,070 | 10/1981 | Montalto et al. | 422/64 X |
| 4,303,611 | 12/1981 | Jessop | 422/65 |
| 4,340,390 | 7/1982 | Collins et al. | 422/64 X |
| 4,341,736 | 7/1982 | Drbal et al. | 422/64 X |
| 4,347,750 | 9/1982 | Tersteeg et al. | 422/64 X |
| 4,430,299 | 2/1984 | Horne | 422/64 |
| 4,452,899 | 6/1984 | Alston | 422/66 X |
| 4,488,810 | 12/1984 | Hatanaka et al. | 422/64 X |
| 4,512,952 | 4/1985 | Blanding et al. | 422/66 X |
| 4,568,519 | 2/1986 | Hamilton et al. | 422/63 X |
| 4,584,275 | 4/1986 | Okano et al. | 422/63 X |
| 4,595,562 | 6/1986 | Liston et al. | 422/65 |
| 4,625,096 | 11/1986 | Fletcher | 422/65 |
| 4,795,613 | 1/1989 | Azuma et al. | |

*Primary Examiner*—Robert J. Warden
*Assistant Examiner*—D. John Griffith, Jr.
*Attorney, Agent, or Firm*—Finnegan, Henderson, Farabow, Garrett and Dunner

[57] ABSTRACT

An apparatus for biochemical analysis wherein a measuring element is conveyed by a conveying device to a dispensing unit for dispensing a substance to be measured into the measuring elements. On the conveyed device a photometric device for subjecting the measuring elements to photometry, and a discharging device for discharging the measuring elements from the conveying device are mounted. The measurement of the elements can be conducted by two or more measuring methods.

17 Claims, 9 Drawing Sheets

F I G. 18 A
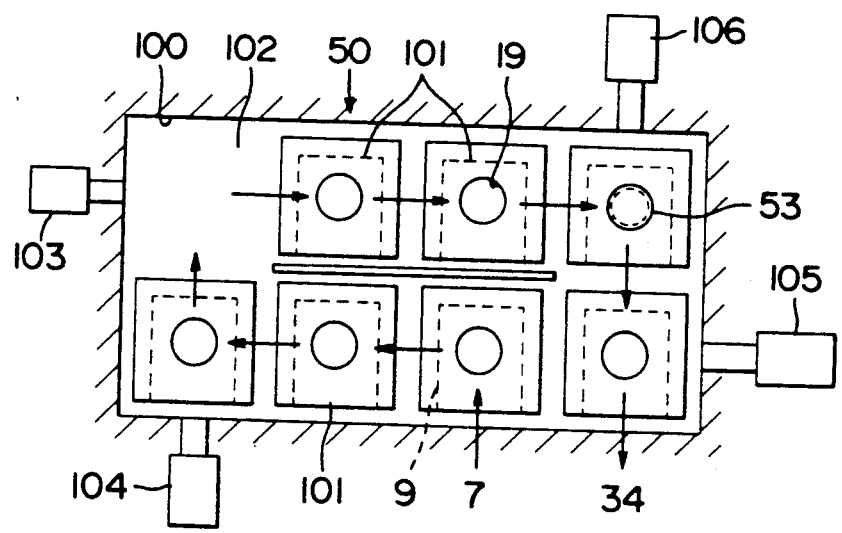
F I G. 18 B
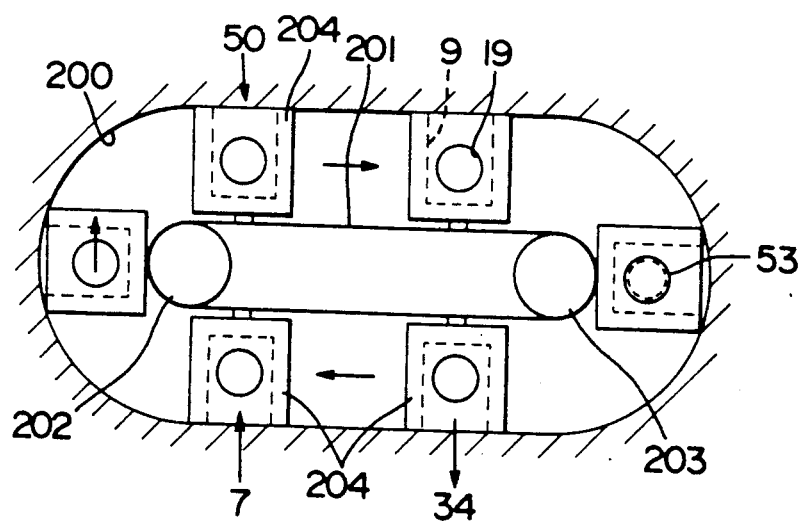

APPARATUS FOR BIOCHEMICAL ANALYSIS

This application is a continuation of application Ser. No. 07/186,682, filed Apr. 21, 1988, now abandoned, which is a continuation of application Ser. No. 07/038/446 filed Apr. 14, 1987, now abandoned, which is a continuation of application Ser. No. 06/833,598 filed Feb. 27, 1986, now abandoned.

BACKGROUND OF THE INVENTION

1. Field of the Invention

The present invention relates to an apparatus for biochemical analysis, and in more detail, it relates to an apparatus for biochemical analysis in which a sample of blood, serum or the like is dispensed, or dropped, into a measuring element impregnated with a reaction reagent and is made to react with the reagent under the prescribed condition of temperature, and the process or the result of the reaction, e.g. a change in the density of color caused by the reaction, is measured so as to analyze chemically the presence or absence of a specified component in said liquid reagent or the content of the component therein, etc.

2. Description of the Prior Art

Conventional apparatuses of this kind are constructed in such a manner that a disk in the circumferential edge part of which fitting grooves for measuring elements are provided at equal intervals is so provided that it can be rotated intermittently, and a unit for dropping a solution to be analyzed and a photometric unit are provided respectively at positions at which said disk is stopped. Solutions to be analyzed, which are dropped from the dropping unit, are conveyed to the photometric unit in sequence as they each pass a time of reaction with the reagent contained in the measuring element, so as to be subjected to photometry. In this construction, the time of stoppage of the disk is determined constantly according to the dropping operation from the sample dropping unit and the speed of photometry in the photometric unit, and the item of each measuring element fitted in the element fitting groove provided in the circumferential edge part of the disk can not be discriminated from one another. Therefore there are problems that the item of the measuring elements employed in one operation must be identical, and that the measuring samples taken from the same person can not be measured simultaneously by an end point method and a rate method determined according to an item of analysis.

Thus there have been apparatuses in which routes for conveying measuring elements are provided by the number of the items of analysis, or a photometric unit branching from a conveyance route is provided for exclusive use for each item of analysis, or a plurality of apparatuses for analysis to each of which a single measuring method is applied are provided together for enabling simultaneous measurement. The former two apparatuses involve a complicated, large-sized and expensive structure as a whole, necessitate high technical skill and are troublesome in maintenance, while the latter one requires a large space for its installation and, moreover, the operation of each unit thereof is complicated.

SUMMARY OF THE INVENTION

The present invention is provided to solve the above-stated problems, and an object thereof is to furnish an apparatus for biochemical analysis which enables the employment of measuring elements for items of different kinds and the execution together with the end point method and/or the rate method in the same conveyance system for measuring different samples, and which has a simple and easy-to-handle structure and is small-sized and inexpensive.

In order to attain the aforesaid object, the apparatus for biochemical analysis according to the present invention is formed of a conveying means for conveying measuring elements, an inserting unit for inserting the measuring elements into said conveying means, a dispensing unit for dispensing, or dropping, a substance to be measured into each measuring element, a photometric means for applying a photometric operation to the measuring elements on said conveying means, and a discharging means for discharging the measuring elements from the aforesaid conveying means, and it is constructed so that the measurement of the elements can be performed by two or more measuring methods.

Other objects and characteristics of the present invention will become more apparent in the following description and the accompanying drawings

BRIEF DESCRIPTION OF THE DRAWINGS

The figures show one embodiment of the present invention, of which:

FIG. 10 is a graph showing the timing of dropping and photometric operation by the rate method;

DESCRIPTION OF THE PREFERRED EMBODIMENT

The present invention will be now described on the basis of one embodiment shown in the attached drawings.

Figure 1:
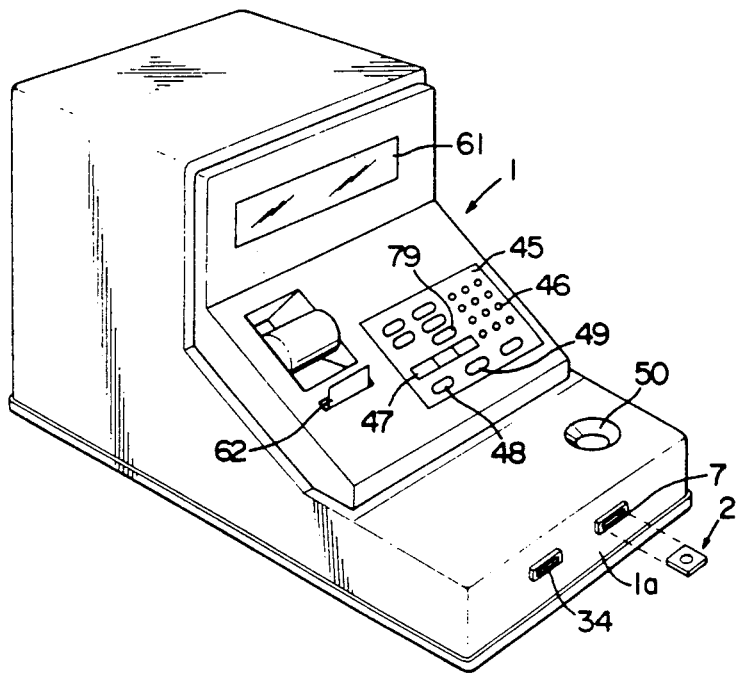
FIG. 1 is a perspective view of the external appearance of the apparatus.
Figure 2:
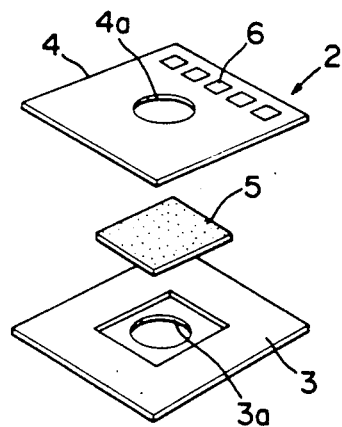
FIG. 2 is an exploded perspective view of a measuring element.
Figure 3:
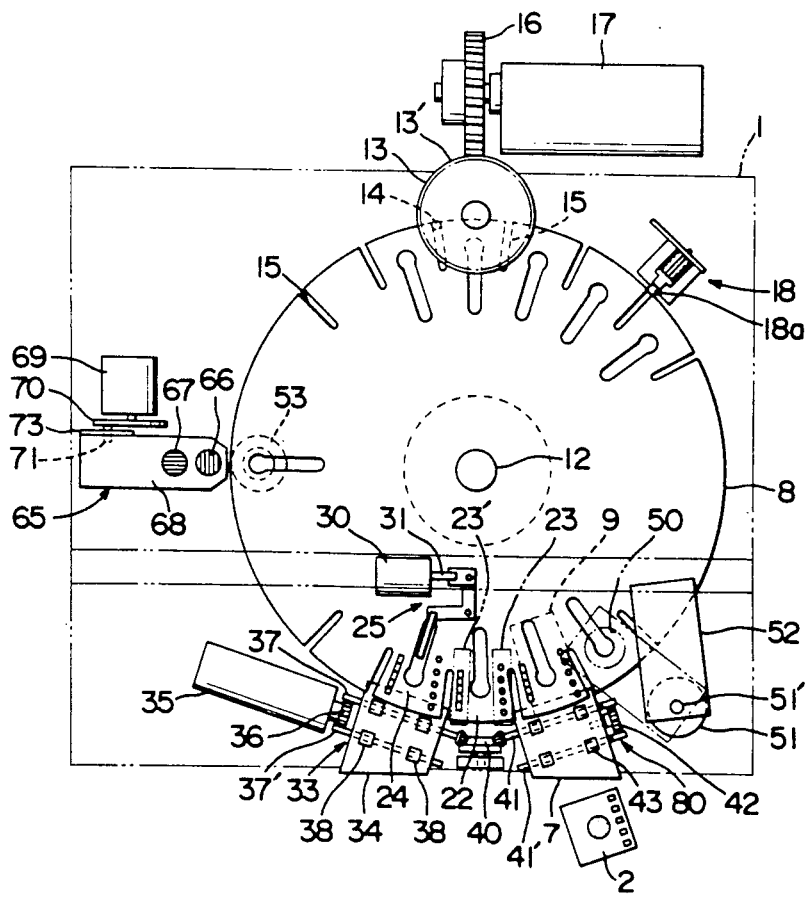
FIG. 3 is a plan view of a disk and the peripheral mechanism thereof.

In FIG. 1, numeral 1 denotes the main body of an apparatus for biochemical analysis, and 2 a measuring element. The measuring element 2 is constructed by interposing a film 5 impregnated with a prescribed reagent between a mount base 3 having a through hole 3a for photometric operation and a mount cover 4 having a through hole 4a for dropping a sample, as shown in FIG. 2, and a code (hereinafter called an item code) 6 for discriminating reagent data (an analyzing item) is recorded (indicated) on the surface of said mount cover 4 in such a manner that it can be discriminated with five bits. Said measuring element 2 is inserted through an element insertion port 7 provided in the front 1a of the aforesaid main body 1, and thereby it is fitted in one of element fitting grooves 9 provided at equal intervals in the circumferential edge part of a disk 8 set in the main body 1, as shown in FIG. 3, through a lead-in means 80, which will be described later. When the measuring element 2 is fitted in one of the element fitting grooves 9, said disk 8 is rotated to and stopped at a position at which the following element fitting groove 9 is made to face the element insertion port 7. As a means of driving said disk 8, in the embodiment, radial grooves 15, each of which is located between the adjacent element fitting grooves 9, are formed in the circumferential edge part of the disk 8, and a rotating wheel 13 having the rotational center at the outer peripheral edge of said disk 8 is provided. Said means is constructed so that a pin 14 fixed in the eccentric position of said rotating wheel 13 can engage with the aforesaid radial groove 15. By this construction, the disk 8 is rotated in such an intermittent manner that it is fed by one pitch through a half rotation caused from the engagement of the pin 14 of the rotating wheel 13 with the radial groove 15 to the disengagement of the former from the latter while it is stopped during a period from the disengagement of the pin 14 from the radial groove 15 to its engagement with the following radial groove 15. Said rotating wheel 13 is linked to a driving motor 17 through a helical gear 16 engaging with the helical gear 13' formed on the peripheral surface of the rotating wheel. Said driving motor 17 operates in response to a pulse signal delivered from a control unit not shown in the figure, making the aforesaid rotating wheel 13 rotate once by one operation thereof. Therefore, the length of the time of stoppage of the disk 8 can be controlled freely by the interval of said pulse signal supplied from the control unit.

Numeral 18 denotes a stopper for securing the stability of the disk 8 when it is stopped, and it is so designed that a spherical body 18a urged by a spring drops partly into one of the aforesaid radial grooves 15.

Figure 4:
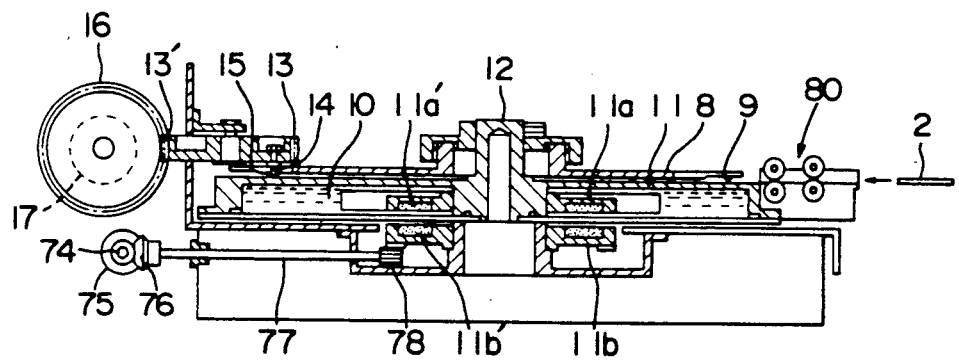
FIG. 4 is a longitudinal sectional front view of the disk and a thermostatic board.

The aforesaid disk 8 is supported axially by a support shaft 12 provided on a thermostatic board 11 in which a heat-retaining liquid 10 is held, as shown in FIG. 4. While said disk 8 is spaced slightly from the top surface of the thermostatic plate 11, the measuring element 2 fitted in the element fitting groove 9 is in direct contact with the thermostatic board 11. This is effective for preheating efficiently the measuring element 2 preserved normally in a cooled state up to the reaction temperature with a sample. The thermostatic board 11 shown herein is so designed that the heat-retaining liquid 10 is heated by a heater (not shown in the figure) provided on the lower side of the bottom plate of the thermostatic board and thus the measuring element is preheated by the heat of the liquid 10. Inside the thermostatic board an agitating blade 11a is provided for securing a uniform distribution of the temperature of the heat-retaining liquid 10 itself. This agitating blade 11a has a permanent magnet 11a' buried therein so that the blade can follow the rotation of a rotary board 11b provided under the thermostatic board 11 by using the magnetic force of a permanent magnet 11b' buried in the rotary board 11b. This rotary board 11b engages with the distal end gear 78 of a second shaft 77 engaged through the base end gear 76 to the gear 75 of a shaft 74 which is coupled to the aforesaid driving motor 17 through an intermediate gear (not shown in the figure), and thus it can rotate simultaneously with the rotation of the disk 8.

Figure 5:
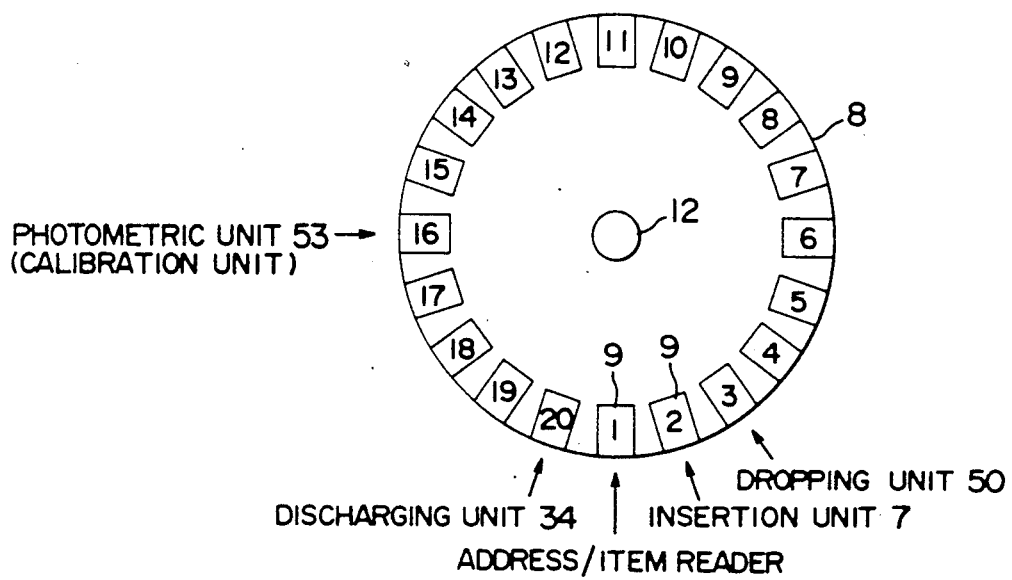
FIG. 5 is a plan view of the disk showing addresses of element fitting grooves.
Figure 6:
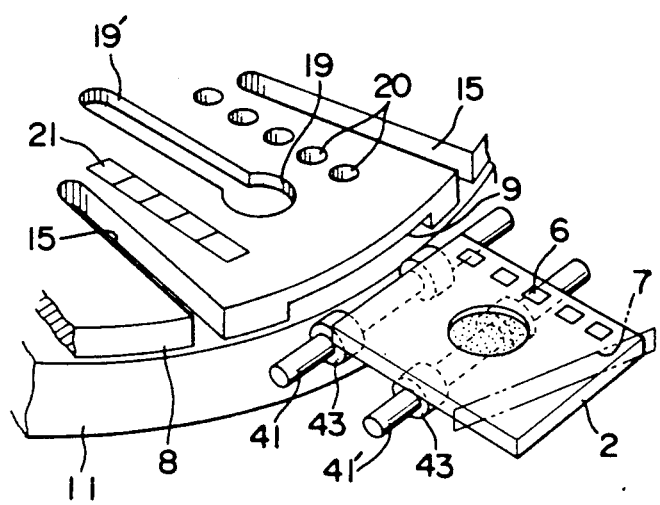
FIG. 6 is a partially enlarged perspective view of the disk.

In the present embodiment, the aforesaid element fitting grooves 9 provided in the circumferential edge part of the disk 8 are twenty in number as shown by marks (1) to (20) of FIG. 5. As shown in FIG. 6, each of the element fitting grooves 9 is provided with a sample dropping window 19, five consecutive see-through windows 20 corresponding to the aforesaid item code 6, and an address code 21 for specifying each of the aforesaid addresses of (1) to (20). Out of these element fitting grooves 9, the groove of the address (1) is reserved for calibration, which will be described later, and thus the measuring elements 2 can be fitted in the grooves of the addresses of (2) to (20), namely nineteen in all. When the present apparatus is powered on, accordingly, the groove of the address (2) comes to the element insertion port 7 after the completion of a prescribed preparatory operation (an operation of confirming the absence of the measuring element in each element fitting groove, which is effective particularly at a power failure or the like). When a first measuring element 2 is inserted into the element fitting groove 9 of the address (2), it is detected by a sensor not shown in the figure, and an insertion finished signal is outputted therefrom to the control unit. Receiving this signal, the control unit makes the aforesaid driving motor 17 operate to move the disk 8 forward by one pitch so as to make an address (3) element fitting groove 9 face the element insertion port 7 of the main body 1, thereby enabling the insertion of a subsequent measuring element 2. As for the measuring element 2 inserted into the address (2), on the other hand, the item code 6 thereof is read, through the see-through windows 20, at a position 22 shown in FIG. 1, located one pitch ahead, by one code reader (reading a code with five bits by using an infrared photosensor, for instance) 23 provided at this position, while an address code 21 indicated on the disk 8 is read simultaneously by another code reader 23' (similar to the above), and thus the item of the measuring element inserted into the address (2) is stored in a memory device not shown in the figure. The items of measuring elements inserted into the addresses (3), (4) and so forth are read and stored sequentially in the same way.

Figure 7A:
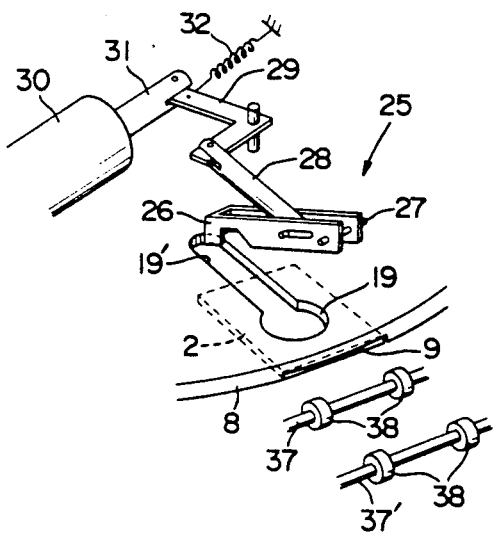
FIGS. 7 A and 7 B are perspective views showing the states of operations of a discharging means.
Figure 7B:
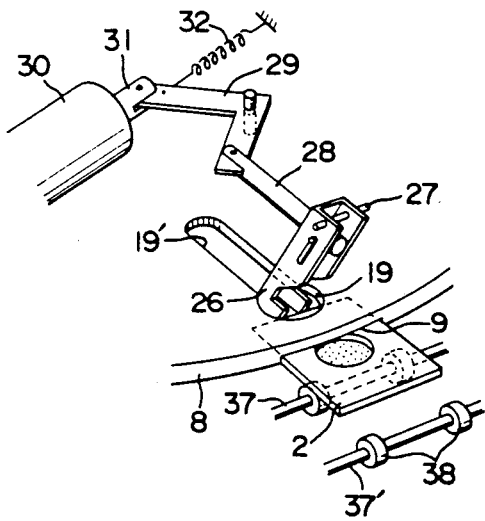
Figure 8:
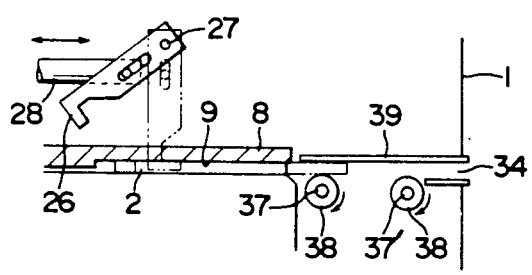
FIG. 8 is a sectional view showing the relationship between a discharging pawl and a delivering means.
Figure 9:
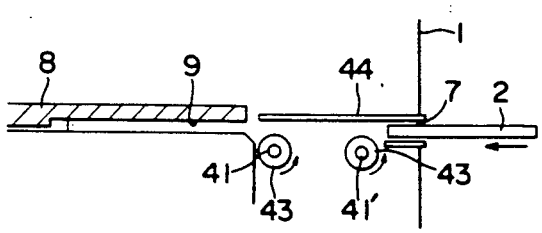
FIG. 9 is a sectional view showing the state of operation of a lead-in means.

A discharging means 25 for discharging the measuring elements 2 from the respective element fitting grooves 9 is provided at a stop position 24 subsequent to the position 22 at which the aforesaid code readers 23 and 23' are set. Said discharging means 25 is provided with a discharging pawl 26 whose base end portion is fitted pivotally through the intermediary of a pin 27 above a long hole 19' formed toward the center of the disk 8 from the aforesaid sample dropping window 19 and whose middle portion is linked to the plunger 31 of a solenoid 30 through the intermediary of a rod 28 and an L-shaped lever 29, and with a spring 32 which pulls said plunger 31 in the projecting direction when the solenoid 30 is not energized. In this construction, the rod 28 is pulled ordinarily by the action of the spring 32 as shown in FIG. 7 A and thereby the distal end of the discharging pawl 26 is lifted up so as not to hinder the rotation of the disk 8. When the solenoid 30 is energized and thereby the plunger 31 is pulled against the spring 32, the rod 28 is pushed out to rotate the distal end of said discharging pawl 26 as shown in FIG. 7 B so that the measuring element 2 in the element fitting groove 9 can be discharged by the pawl operating through the aforesaid long hole 19'. The measuring element 2 discharged by this operation of the discharging pawl 26 is delivered out of the main body 1 from an exit 34 provided in the front of the main body 1, through a delivering means 33. This delivering means 33 is provided with two parallel shafts 37 and 37' which are driven in the direction of delivery by a gear 36 fixed to the output shaft of a driving motor 35, as shown in FIG. 3, and it is so designed that the measuring element 2 can be held between friction rollers 38, which are fixed by twos to said shafts 37 and 37' respectively, and an upper-side guide plate 39, and delivered out thereby as shown in FIG. 8. The aforesaid lead-in means 80 provided between the aforesaid element insertion port 7 and the element fitting groove 9 of the disk 8, on the other hand, is provided with a shaft 41 connected to the shaft 37, one of the two shafts of the aforesaid delivering means 33, through the intermediary of a linking gear 40, and with a shaft 41' linked parallel to said shaft 41 through the intermediary of an intermediate gear 42, and friction rollers 43 are fixed by twos to these shafts 41 and 41' respectively. By this construction, the measuring element 2 inserted through the element insertion port 7 can be held between these rollers 43 and an upper-side guide plate 44 and fed into the element fitting groove 9 as shown in FIG. 9.

An operating panel 45 of the present apparatus is provided on the top surface of the aforesaid main body 1. This operating panel 45 is provided with numeric keys 46 for inputting the specimen number as occasion calls when the measuring element 2 is inserted into the element fitting groove 9 of the disk 8, a switch 47 for selecting a measuring method, a switch 48 for starting the dispensing of a sample, a switch 49 for ending the dispensing thereof, etc.

When the measuring element 2 is inserted into the element fitting groove 9 through the aforesaid element insertion port 7, the disk 8 is moved forward in response to an output signal delivered from a sensor detecting said measuring element 2, and simultaneously a first timer, not shown in the figure, is made to operate. This first timer is provided for controlling a time interval from the insertion of one measuring element to that of a subsequent element, e.g. an interval from the insertion into the address (2) to that into the address (3), or from the insertion into the address (3) to that into the address (4). The set time of said first timer is determined normally in consideration of a time required from the insertion of one measuring element 2 into the element fitting groove 9 to the arrival thereof at the reaction temperature (about 37° C.) through absorption of the heat of the thermostatic board 11. In the present embodiment, this time is determined as three minutes after the last measuring element is inserted. Concretely, the first timer starts counting of three minutes on the insertion of the measuring element 2. When a subsequent measuring element is inserted, however, the count made until then is cleared, and the counting is started afresh. Accordingly, when some measuring element is inserted and no subsequent measuring element is inserted within three minutes thereafter, the first timer operates to deliver an insertion end signal to the control unit. Based on this signal, the control unit determines that no subsequent insertion is made and that the measuring element inserted just before the reception of said signal is the last one, and drives the disk 8 to put forward the reserved address (1) with no measuring element 2 inserted therein to a photometric unit 53, which will be described later. After a calibration, which will be described later, is ended in said photometric unit 53, the measuring element 2 fitted in the element fitting groove 9 of the address (2) is conveyed rapidly to a dropping unit 50 which is provided on the front upper side of the main body 1.

Figure 10:
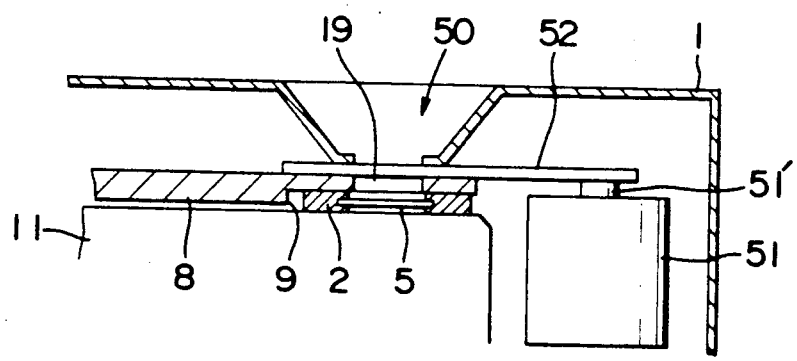
FIGS. 10 A and 10 B are sectional views of a sample dispensing unit showing the operation of a shutter.
Figure 10:
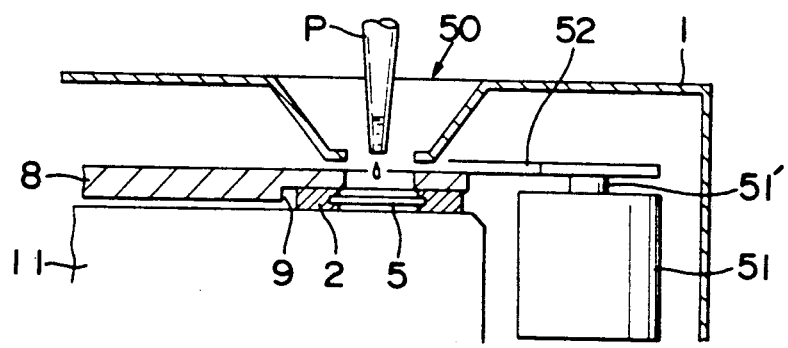

The aforesaid sample dispensing unit 50 is provided with a shutter 52 whose base end portion is fixed to the output shaft 51' of a motor 51 as shown in FIG. 10. This shutter 52 is so constructed that it shuts up the dispensing unit 50 ordinarily as shown in FIG. 10 A and opens it only when a sample is dispensed, as shown in FIG. 10 B, so as to prevent the temperature inside the main body 1 from being affected by the outside air temperature. This shutter 52 is so designed that it is opened by pushing a depressing start switch 48 on the operating panel 45 of the main body 1 when a sample is dispensed for the first time, and is opened automatically thereafter. The shutting operation of the shutter 52 after the dispensing of the sample is ended is conducted by depressing a dispensing finish switch 49. Simultaneously when this dispensing end switch 49 is depressed, second, third and fourth timers, not shown in the figure, are made to operate, while a fifth timer is made to operate interlocking with the opening operation of the shutter.

The aforesaid second timer controls a time from the end of dropping to a photometric operation, which will be mentioned later. The time is thereby controlled for each measuring element in such a manner, for instance, that it is set to be seven minutes when a given measuring element of which the dispensing is ended has properties to be measured by the end point method, and two and four minutes when said element has properties to be measured by the rate method. Accordingly, this second timer is provided in the same number (nineteen in the present embodiment) with the measuring elements which can be inserted into the respective element fitting grooves 9. The selection of the measuring method out of the end point method and the rate method is made in accordance with an analytic item, and the method thus selected is stored beforehand in the memory device when the item code 6 is read.

The third timer controls a time from the end of the dispensing of a sample into a first measuring element (the measuring element put in the address (2), for instance) to the application of the photometric operation thereto, i.e. a time allowing the dispensing. For instance, it controls the time to be seven minutes when the first measuring element should be measured by the end point method, and to be two minutes when said element should be measured by the rate method, making it impossible to conduct the dispensing thereafter. The time interval of seven minutes or two minutes is set for the photometric operation, and thus the actual time-up of this timer comes about 30 to 40 seconds before the termination of the aforesaid time interval, in other words, the actual time-up of the timer is set at the time of 6 minutes 20 to 30 seconds after the completion of the dropping in the former case, and at the time of 1 minute 20 to 30 seconds thereafter in the latter case, in consideration of a time required for conveying the measuring element to the photometric unit 53. With the time-up, the third timer holds the aforesaid shutter 52 shut, making it impossible to conduct the dispensing thereafter. In the present embodiment, therefore, a stop watch (not shown in the figure) is made to operate 30 seconds before the termination of the time interval (the time-up of the third timer), so that the remaining time interval can be displayed by countdown, such as 30, 29, 28 . . . , for instance, in a display 61.

The fourth timer controls the time interval from the closing of the shutter 52 upon completion of dispensing of a sample into one measuring element to the time the shutter is automatically opened. While the time interval controlled by this timer can be determined freely according to the speed of operation of an operator within the limits allowed by the third timer, its regulation will be sufficient in general to be about 30 to 15 seconds.

The fifth timer controls a time interval from the opening of the shutter to prevent the temperature of measuring elements from changing appreciably by leaving open the shutter 52 for a long time. An alarm is given with the time-up of this timer, at the same time the shutter is closed automatically. The time interval controlled by this fifth timer is set to be relatively short, e.g. 10 seconds approximately, relating to its function. Therefore it is advisable to give some signal sound at an interval of 1 second, for instance, to inform the operator the passage of time, and this timer is provided with a sounding device (not shown in the figure) for this purpose. When the dispensing is ended within 10 seconds after the opening of the shutter and the dispensing end switch is depressed, the shutter is closed. When the shutter 52 is closed with the time-up of the fifth timer, on the other hand, it can be opened again by depressing the dispensing start switch 48 unless the aforesaid third timer gets to the time-up.

With the time-up of the third timer, the dispensing of the sample is made impossible thereafter, as described above, even when the sample is not yet supplied to all the measuring elements fitted in the element fitting grooves 9 of the disk 8, and consequently only the measuring elements supplied with the sample are forwarded sequentially to the photometric unit 53 to be subjected to the photometric operation. In other words, if the third timer gets to the time-up when the dispensing of the sample is ended for the elements at the addresses (2) to (6), only these elements are subjected to the photometric operation. After the photometry of the address (6) measuring element and another calibration thereof are ended, an address (7) is sent again to the sample dispensing unit, and the same processes as described above are executed over again.

Figure 11:
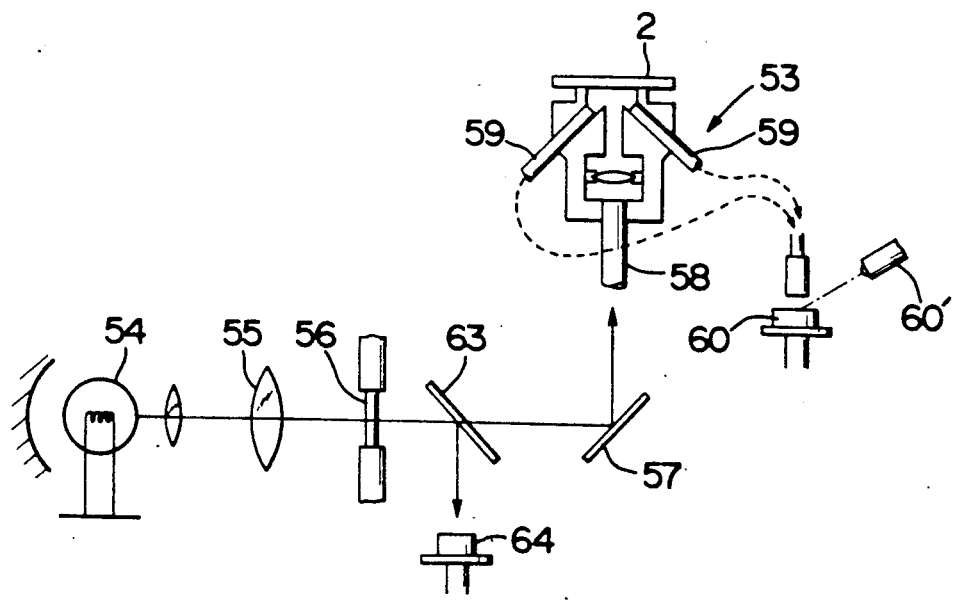
FIG. 11 is a sectional view of the construction of a photometric unit.

The aforesaid photometric unit 53 measures the state of progress or the result of the reaction of the sample in the measuring elements with a reagent in the film thereof by a method of measuring optically a change in the density of color caused by the reaction. This unit is constructed so that, as shown in FIG. 11, a ray of light generated by a light source 54, such as a halogen lamp, is turned into a photometric ray of light having a prescribed wavelength (a wavelength corresponding to an analytic item) by a lens 55 and a switchable filter 56. Said photometric ray is reflected by a mirror 57 and applied onto the measuring surface of the measuring element 2 (the back surface of the element) through an optical fiber 58, a reflected ray of light therefrom is transmitted to a light-receiving element 60 through an optical fiber 59, the reflection density of this ray, i.e. the optical density thereof, is measured by a densitometer (not shown in the figure), the density of a material thus obtained is collated with a working curve prepared for each analytic item to find a measured value, and this is displayed as a numeric value in the display 61 of the main body 1, while it can be printed on rolled recording paper 62. The aforesaid filter 56 is of a rotary type, and can be substituted for a shutter.

The aforesaid light-receiving element 60 employed in this photometric unit 53 shows a delay in its reaction in some of the cases when it receives a light abruptly in the photometric operation. In order to compensate this delay, the present embodiment is given a construction in which a light from an auxiliary light-emitting source 60' is applied constantly to the light-receiving element 60 to apply some bias thereto so that this element can react immediately when the photometric operation is actually conducted (the auxiliary light-emitting source 60' is turned off on this occasion).

Moreover, a transparent glass plate 63 tilted at an angle of 45 degrees is provided in the optical path of the aforesaid photometric ray of light so that a part of light reflected by this transparent glass plate 63 can be supplied as a reference to a compensation circuit through a light-receiving element 64 and that an error in the measured value due to the fluctuation with time of the quantity of the photometric ray of light etc. can be eliminated as far as possible. This light-receiving element 64 may also be provided with such an auxiliary light-emitting source as stated above in reference to auxiliary light-emitting source 60'.

Figure 12A:
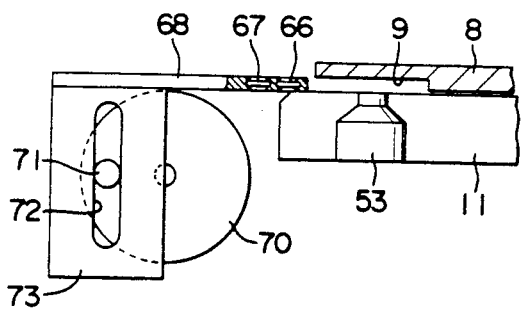
FIGS. 12 A, 12 B and 12 C are sectional views showing the states of operations of a calibration mechanism.
Figure 12B:
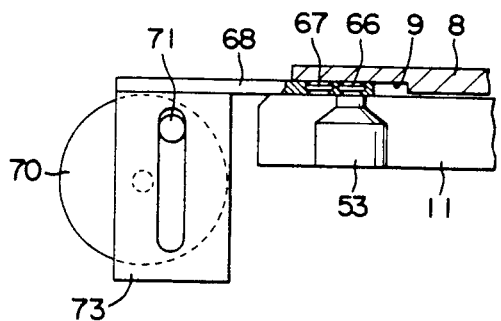
Figure 12C:
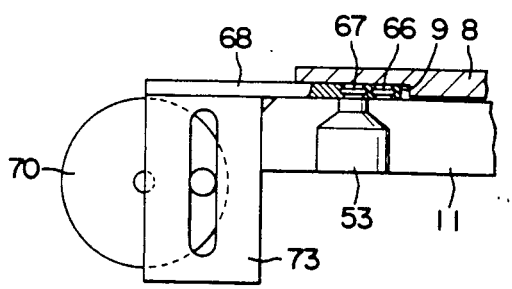
Figure 13:
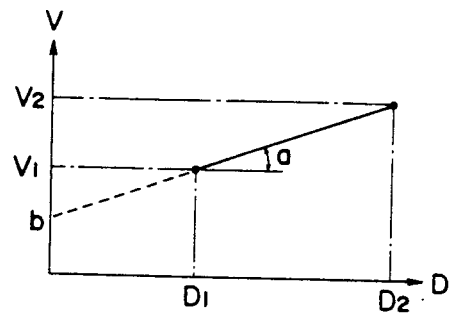
FIG. 13 is a graph for explaining calibration.

The densitometer employed in the aforesaid photometric unit 53 does not always give a stable value. Therefore it is necessary to conduct calibration within a time before and as much nearer to the actual photometry of the measuring element as possible. For this purpose, the aforesaid photometric unit 53 is provided with a calibration mechanism 65 as shown in FIG. 3. This mechanism has a construction in which a slide 68 equipped with two kinds of reference plates, i.e. a first reference plate 66 showing a low optical density value obtained beforehand by a certain photometric device capable of measuring an optical density accurately and a second reference plate 67 showing a high optical density value obtained also by said device, is provided, and this slide 68 is fitted to an operating body 73 which is made to engage, through a long hole 72, with a pin 71 provided at an eccentric position of a disk 70 fixed to the output shaft of a motor 69 so that it can conduct a linear reciprocating motion with the rotation of said disk 70. Said calibration mechanism 65 starts operation when the reserved address (1) element fitting groove 9 comes to a position corresponding to the photometric unit 53 after the sequential insertion of measuring elements into the address (2) and subsequent element fitting grooves and the time-up of the first timer. Until then, the slide 68 is set back from the disk 8 as shown in FIG. 12 A. With this start of operation, the motor 69 rotates the disk 70 as shown in FIG. 12 B and stops it. Thereby the slide 68 is advanced together with the operating body 73 and inserted into the address (1) element fitting groove 9, so that the first reference plate 66 can be positioned on the photometric unit 53 as shown in FIG. 12 B. After said first reference plate 66 is subjected to the photometric operation, the motor is operated again to advance further the slide 68 and thus to position the second reference plate 67 on the photometric unit 53 as shown in FIG. 12 C. By the photometry of these first and second reference plates 66 and 67, optical density values D1 and D2 corresponding to a low voltage value V1 and a high voltage value V2 delivered from the densitometer employed in the given photometric unit 53 respectively can be obtained. Accordingly, a straight line tilted at a certain angle can be obtained by setting a voltage value V and an optical density D on the axes of ordinate and abscissa respectively and by finding the co-ordinates thereof as shown in FIG. 13. When the tilt angle of said straight line is denoted by a and the point of intersection of this line and the axis of ordinate by b, the relationship $$V = a \cdot D + b$$

is established. Therefore, an optical density Dx at the time when a voltage value Vx is obtained from the actual photometry of the measuring element can be calculated as $$Dx = (Vx - b)/a$$

according to the aforesaid formula. Thus, the optical density is calibrated to have a correct optical density value, and a density value of a material can be determined as a correct value.

After the calibration is executed by the aforesaid calibration mechanism 65, the measuring elements, beginning with the one at the address (2), are conveyed sequentially to the dropping unit 50, at which a sample is dropped thereinto as described previously.

Next, the sequence of the operations of the above-described embodiment will be described with reference to FIG. 14

First, a power switch is turned ON (step I). Whether or not measuring elements are left in the element fitting grooves 9 of the disk 8 is then checked up by a sensor provided corresponding to the element insertion port 7. If any measuring element is left therein, the element fitting groove at the address at which said element is left is moved forward to a position at which the discharging means is provided, and a discharging process (step II) is executed. After all the element fitting grooves 9 are checked-up, the address (2) element fitting groove 9 is moved to the position corresponding to the element insertion port 7 (step III). Then, the operator operates a measuring-method selecting switch 47 of the operating panel 45 provided on the top side of the main body 1, so as to select a mode, as occasion calls (step IV). There are three kinds of modes to be selected, i.e. a mode in which the end point method alone is executed, a mode in which the rate method alone is executed, and a mixed mode in which both of these end point and rate methods can be executed. Since the apparatus is set to the mode of the end point method unless these selecting switches are operated, the switches are to be operated in the case when any one of the two kinds of modes other than the mode of the end point method is selected, or in the case returning is again to this mode after the other modes are selected.

Next, the operator operates a numeric key 46 on the aforesaid operating panel 45 to input a specimen number (step V). This input of the specimen number is required for discrimination when specimens are taken from several persons, and so it is not always required when the specimen is taken from one and the same person.

After the above-stated operation is completed, measuring elements 2 are inserted through the element insertion port 7 (step VI). When a first measuring element is inserted into the address (2) element fitting groove 9, it is detected by a sensor, the disk 8 is moved forward by one pitch, and the address (3) element fitting groove 9 is brought to the insertion port 7 of the main body 1. While the insertions are conducted one after another in this way, they must be performed within a time interval (3 minutes) controlled by the first timer. The measuring element inserted into the element fitting groove 9 is forwarded to a next position, and the item code 6 and the address code 21 thereof are read thereat by the code readers 23 and 23' respectively. These codes are stored respectively in a memory device not shown in the figure. In the case when these insertions are made for the measurement by the mode of the end point method, for instance, an "error display" appears on the display if any measuring element to be measured by the selection mode of the measuring method differ from said mode is inserted. On such an occasion, the erroneous measuring element is conveyed to the discharging unit and discharged therefrom immediately. After the discharge, the emptied element fitting groove 9 is turned round to the element insertion port 7 again, and a subsequent measuring element is inserted. This discharging process is executed for any measuring element unsuitable because of false printing of a bar code, defect or the like other than the difference in the mode. In addition, a cancel switch 79 is provided on the aforesaid operating panel 45 so that the same operation as the above can be conducted by depressing it when a measuring element is inserted erroneously.

When the aforesaid first timer gets to the time-up with the insertion of all measuring elements to be subjected to photometry, the control unit determines that no further insertion is made. Based on the determination, the reserved address (1) in which no measuring element 2 is inserted is forwarded to the photometric unit 53, and the calibration mechanism 65 provided for said photometric unit 53 is operated to execute calibration (step VII).

Then, the measuring element 2 set in the address (2) element fitting groove 9 is conveyed rapidly to a position just under the sample dispersing unit 50. The arrival of this measuring element at the dispensing unit 50 is informed by a buzzer or the like, while the specimen number, the analytic item, etc. of the element are displayed on the display 61. Checking up this display, the operator takes a necessary sample by a pipette P and then depresses the dispensing start switch 48 on the operating panel 45. In the meantime, the measuring element 2 is heated generally to the reaction temperature by the heat of the thermostatic board 11, and thus the dispensing of the sample can be executed at any time. After the shutter 52 is opened by said operation of depressing the dispensing start switch 48, the sample is dispensed (step VIII). After the dispensing of the sample is ended, the operator depresses the dispensing end switch 49. Thereby the shutter 52 is closed and the disk 8 is rotated to move the measuring element at the subsequent address to the position just under the dispensing unit. When the dispensing end switch 49 is depressed, the following timers operate: the second timer controlling the time from the end of the dispensing to the photometric operation for each measuring element; the third timer controlling the time from the dispensing of the first measuring element to the photometry thereof (a dispense enabling time); the fourth timer controlling the time until the next dispensing; and the fifth timer controlling the time from the opening of the shutter so as to prevent the shutter 52 from being left opened too long a time.

With the time-up of the aforesaid third timer, measuring elements, beginning with the measuring element at the address (2), are conveyed sequentially to the photometric unit 53, where the photometric operation is conducted (step IX). As the results, the serial numbers, the item, measured values, etc. of one batch (the measuring elements inserted into the element fitting grooves on the disk) are displayed in the display 61, the same results are printed on rolled recording paper 62.

When the third timer gets to the time-up before the sample is dispensed in all the measuring elements, only the measuring elements having received the sample by that time point are subjected to the photometry, and after the completion thereof, the remaining measuring elements are subjected to the processes from the step VII to the step IX.

When the photometry is completed for all the measuring elements in this way, the address (2) element fitting groove 9 is moved to the position at which the discharging means 25 is provided, and there the measuring elements having been subjected to the photometry are all discharged sequentially (step X). After the completion of discharge, the address (2) is forwarded to the insertion port 7 (step III), thus one round of analytic operations being ended. When a second round of analytic operations is conducted thereafter without turning the power switch OFF, the operations begin with the aforesaid step IV.

Figure 19:
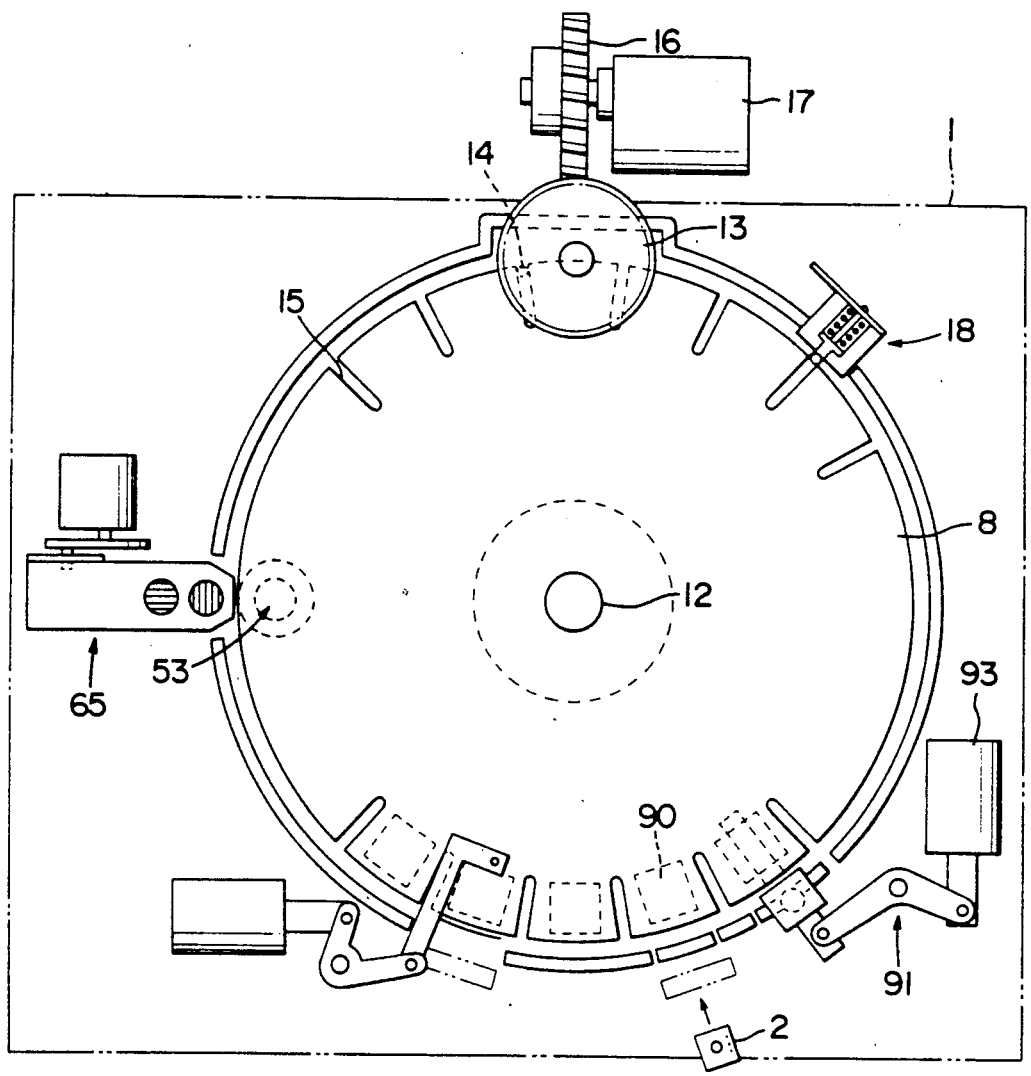
FIG. 19 is a plan view of the other embodiment of the present invention.
Figure 20:
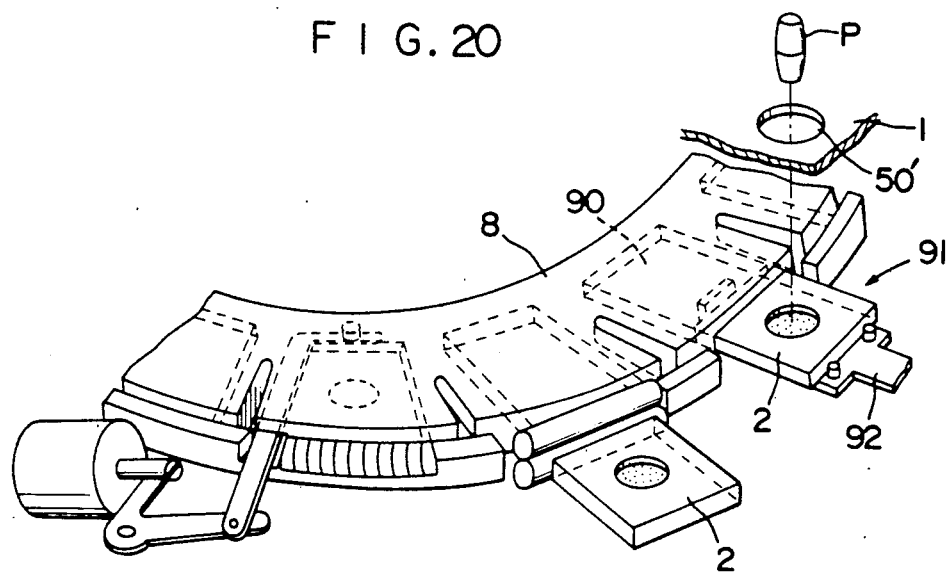
FIG. 20 is a partially enlarged perspective view of the apparatus shown in FIG. 19.

Another embodiment of the present invention will now be explained with reference to FIGS. 19, 20, 21 A and 21 B.

In this embodiment the sample dispensing window 50' is positioned out of the disk 8. The sample dropping is carried out by moving the measuring element 2 positioned on an element holding portion 90 under the sample dispersing window 50' and then moving the measuring element 2 back on the element holding portion 90.

FIGS. 21 A and 21 B show element reciprocating means 91 for reciprocating the measuring element 2 between the element holding portion 90 and the sample dispensing window 50'.

FIG. 21 A shows such a state that the measuring element 2 is positioned on the element holding portion 90 after or before the sample dropping and FIG. 21 B shows such a state that the measuring element 2 is moved under the sample dispensing window 50' after being taken out of the element holding portion 90.

The element reciprocating means 91 comprises an element moving plate 92 for holding the measuring element 2 and reciprocating it between the element holding portion 90 and the sample dispensing window 50', a solenoid 93 for driving said element moving plate 92, and an intermediate lever 94 rotated centering about a lever shaft 95 fixed on the main body 1. The element moving plate 92 has a shutter plate 96 to be positioned under the sample dispensing window 50' for closing the latter after and before the sample dispensing other than the sample dispensing state. The upper surface of the shutter plate 96 is colored with red paint for indicating that sample dropping is impossible.

When the preheated measuring element 2 reaches the position shown in FIG. 21 A the solenoid 93 is energized to move the measuring element 2 to the position shown in FIG. 21 B. Specifically, the intermediate lever 94 is rotated in the counter-clockwise direction centering around the lever shaft 95, the measuring element 2 is drawn from the element holding portion 90, and said shutter plate 96 is retracted from the sample dispensing window 50' when the solenoid 93 is actuated, so that the through hole 4a of the measuring element 2 for the sample dispensing is instead positioned just below the sample dispensing window 50'.

In this state, if a sample dispense ending button mounted on the main body 1 is depressed the solenoid is de-energized and the element reciprocating means 91 is returned to the position shown in FIG. 21 A by an action of a spring provided at the inside or outside of the solenoid 93, so that the measuring element 2 which has received the sample dispensed is returned to and held by the element holding portion 90 again.

Figure 15:
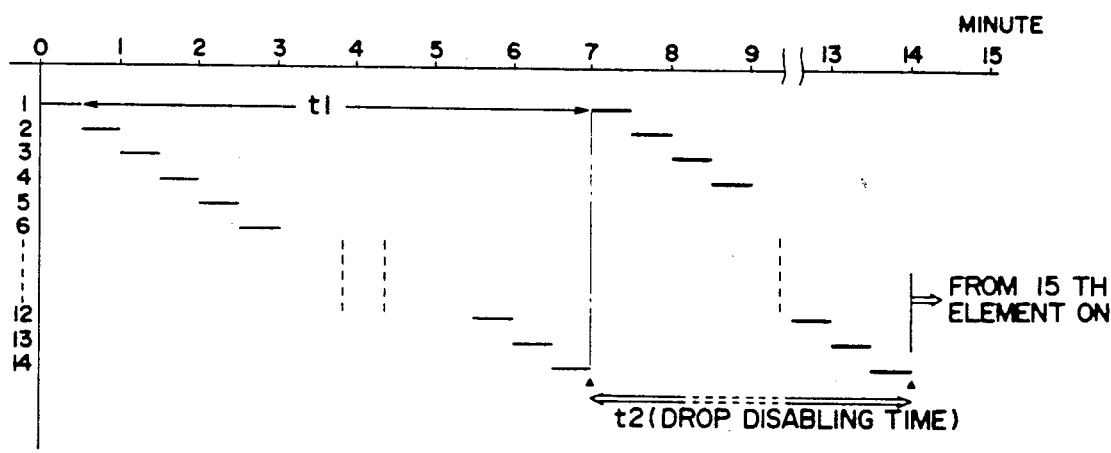
FIG. 15 is a graph showing the timing of dropping and photometric operation by the end point method.

FIG. 15 is a graph showing a sample dispense timing and a photometric timing in the case of the end point mode in which only the end point method is applied. The time (minutes) is shown on the axis of abscissa, and the number of measuring elements on the axis of ordinate. In the graph, a thin horizontal bar represents the length of a time (a dispensing interval) required for moving the measuring element to the sample dispensing station and finishing the dispensing of a sample into the element, while a thick horizontal bar represents the length of a time (a photometric interval) required for moving a measuring element to the photometric station and finishing the photometric operation.

This graph shows that, when said dispensing interval and the photometric interval are set to be just 30 seconds respectively, the time t1 from the end of dispensing of the sample into a first measuring element to the beginning of photometry thereto is 6 minutes 30 seconds, that since this time is the sample dispense enabling time, the sample can be dispensed into the second to fourteenth measuring elements during said time, and that the time t2 from said end of dropping to the time point of fourteenth minutes on the axis of abscissa, at which the photometric operation beginning seven minutes later for the first to fourteenth measuring elements is ended, is a sample dispense disabling time. While the dispensing interval and the photometric interval are set on 30 seconds respectively in the present graph, if said intervals are set on 15 minutes respectively twice as many as dispensings are enabled, by a simple calculation, by the ending point of the aforesaid dispense disabling time, and the time until the end of photometry can be also shortened.

Figure 16:
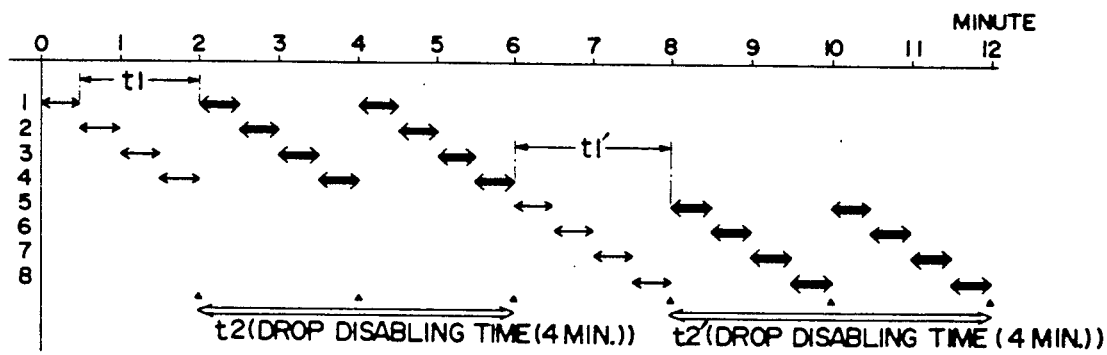

FIG. 16 is a graph showing a sample drop timing and a photometric timing in the case of the rate mode in which only the rate method is applied. The time (in minutes) is shown on the axis of abscissa and the number of measuring elements on the axis of ordinate in the same way as the above.

In this graph, a thin horizontal bar with arrows at both ends represents the length of a time (the dispensing interval) required by the end of dispensing for one measuring element including moving time to the sample dispensing unit, while a thick horizontal bar with arrows at both ends represents the length of the time (the photometric interval) required by the end of photometry for one measuring element including moving time to the photometric unit.

The present graph shows that, when said dispensing interval and the photometric interval are set on just 30 seconds respectively, the time t1 from the end of dispensing of a sample into a first measuring element to the application of photometry thereto is 1 minute 30 seconds, that since this time is the sample dispense enabling time, the sample can be dispensed into the second to fourth measuring elements during said time, that the time t2 required by the end of the photometric operation executed two minutes later for these second to fourth measuring elements and of the photometric operation executed four minutes later is the dispense disabling time, that the time of 2 minutes between the time points of 6 and 8 minutes on the axis of abscissa after the end of said dispense disabling time t2 is another dispense enabling time t1' and the dispensing can be conducted for the fifth to eighth measuring elements during this time, and that the time of 4 minutes between the time points of 8 and 12 minutes is another dispense disabling time t2'.

Figure 17:
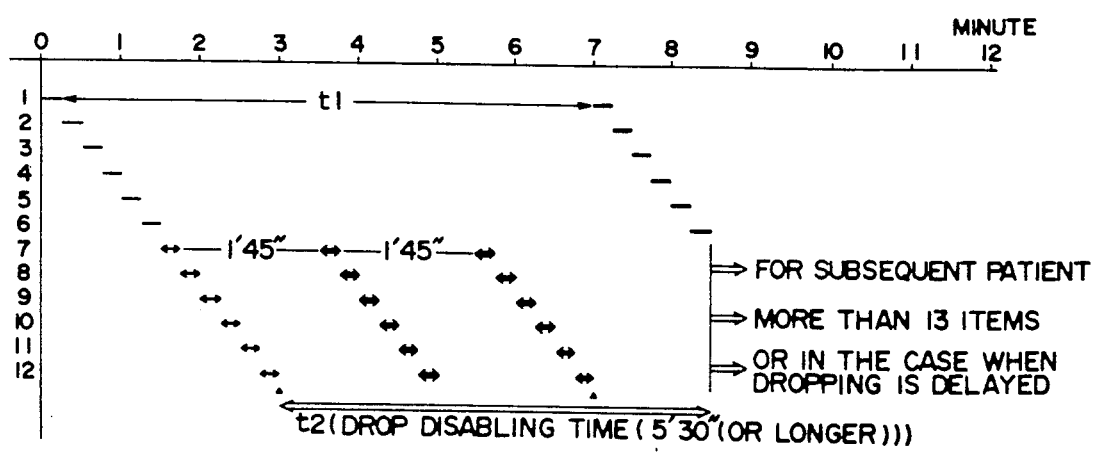
FIG. 17 is a graph showing the timing of dropping and photometric operation by the mixing process of the end point method and the rate method.

FIG. 17 shows the case of the mixed mode of the end point and rate methods. In the same way as the above, the time (in minutes) is shown on the axis of abscissa and the number of measuring elements on the axis of ordinate. In this figure, a thin horizontal bar represents the sample dispensing interval in the end point method, while a thick horizontal bar represents the photometric interval in the same method. Moreover, a thin horizontal bar with arrows at both ends represents the sample dispensing interval in the rate method, while a thick horizontal bar with arrows at both ends represents the photometric interval in the same method.

The present graph shows that a sample is dispensed sequentially into the first to sixth measuring elements of the end point method at an interval of 15 seconds, and that the dispensing of the sample and the photometric operation for the seventh to twelfth measuring elements of the rate method are ended during the dispense enabling time t1 from said dispensing for the first to sixth elements to the photometric operation for the first elements. In this case, accordingly, all the analysis of the first to twelfth measuring elements can be completed at a stretch by a time of 8 minutes 30 seconds later at which the photometry of the measuring elements of the end point method is ended. In other words, the mixed mode of the end point and rate methods enables the saving of the time for dispensing and photometry by executing dispensing and photometric operations for the elements of the end point method first, and by utilizing the dispense enabling time by the time of application of photometry thereto for the execution of these operations for the elements of the rate method.

Regarding the apparatus for biochemical analysis in which the disk, a means for conveyance, with the measuring element fitting grooves arranged in the circumferential edge part is provided so that it can rotate intermittently at each angle corresponding to each of said fitting grooves, and in which the sample dispensing unit and the photometric unit are provided at the stopping positions of said disk so that the measuring elements in which a sample dispensed thereinto by the dispensing unit has passed the time of reaction with a reagent contained in the elements can be conveyed sequentially to the photometric unit to be subjected to the photometric operation, the above-described embodiment exemplifies the apparatus for biochemical analysis which is equipped with (a) a means of selecting two or more measuring methods for the aforesaid measuring elements, (b) a means of detecting the address of the position of the fitting groove of the disk corresponding to the set position of the measuring element inserted thereinto, (c) a means of inputting the time of dispensing of a sample (which comprises the dispensing end switch and a dispense detecting means not shown in the figures), and (d) a means of controlling the disk, which computes and processes signals from the aforesaid means (a) to (c) and controls the driving of the disk.

In the case when the measuring elements are conveyed by a circulation-type conveying means, in which the aforesaid disk 8 is employed, the means for conveyance is not limited to the disk, and other appropriate means are employed in some cases. FIGS. 18 A and 18 B show other typical means therefor. FIG. 18 A shows a circulation-type conveying means in which a pusher device is employed. In this figure, numeral 100 denotes a rectangular external frame, and 101 plate-shaped shoes which are arranged with a space 102 for one shoe left open so that the shoes can be circulated in a square way within said external frame 100. Each of said shoes 101 has a groove for fitting the measuring element 2 and is provided with a sample dispensing window 19 on the upper side and a window for photometry (not shown in the figure) on the lower side. Numerals 103 to 106 denote pushers provided at four corners of the external frame 100 for pushing the shoes 101 in the direction of the advance thereof. The pushers 103 to 106 are altered sequentially in the operation in such a manner that, when the shoes 101 are in such a state as shown in the figure (that is, the aforesaid space 102 is located just before the pusher 103), the pusher 104 is operated to push out the shoe 101 located just before it, and then the pusher 105 and subsequently the pushers 106 and 103 are operated. Thereby the shoes 101 are circulated as indicated by arrows within the external frame 100. Therefore, by providing a unit 7 for inserting the measuring elements 2, a sample dispensing unit 50, a photometric unit 53 and a discharging unit 34 in the course of the circulation, the same operations as shown in the above-described embodiment can be conducted.

FIG. 18 B shows a system in which measuring elements can be conveyed in a long-elliptical circulation. In the figure, numeral 200 denotes a long-elliptical external frame, and 201 an endless member stretched between two shafts 202 and 203, while 204 denotes a shoe which is supported at one point by the endless member 201 and provided with a groove 9 for fitting the measuring element. In this system, the shoes 204 can be moved in the direction of arrows by driving intermittently either one of the shafts 202 and 203 between which the endless member 201 is stretched, and the same operations as shown in the above-stated embodiment can be performed by providing the unit 7 for inserting the measuring element 2, the sample dispensing unit 50, the photometric unit 53 and the discharging unit 34 in the course of movement of the shoes in the same way as in FIG. 18 A.

Any one of the above-described embodiments shown as those of the disk-conveying type, the pusher-conveyed type and the endless member-conveyed type respectively has an arrangement structure in which the unit 7 for inserting the measuring elements, the sample dispensing unit 50, the photometric unit 53 and the discharging unit 34 are provided in the route of circulating conveyance. In these cases, one measuring element or a group of measuring elements are not conveyed separately from another when two or more prescribed numbers of the elements are measured. In other words, every one of the aforesaid embodiments has a construction in which a unitary conveyance system in which the movement of any measuring element affects necessarily the movements of all or a part of the other measuring elements except for the insertion and discharge thereof is employed, and in which the measuring methods different from one another are applied. Therefore, they are so constructed as to make the cost of manufacture much more inexpensive than an apparatus in which a number of systems of means for conveyance are provided.

EFFECT OF THE INVENTION

As is described above, the present invention enables the employment of measuring elements for the items of different kinds and the analysis using samples taken from different persons, and further the mixed execution of the end point method and the rate method on one and the same disk.

Moreover, it has such a variety of effects that the apparatus according thereto has a simple structure as a whole, can be manufactured inexpensively, is small in size, occupies no large space, requires no special technical skill in operation, is easy to handle, facilitates maintenance, etc.

F I G. 21A
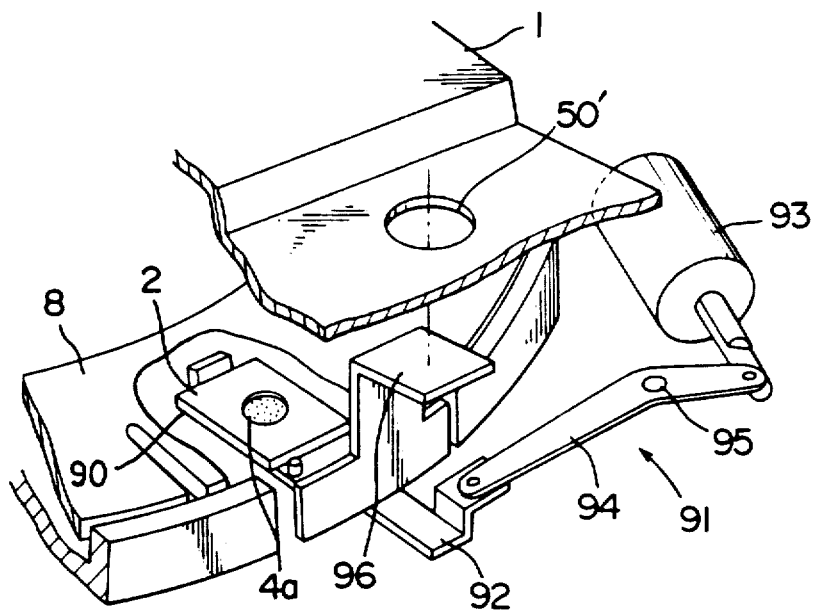
F I G. 21B
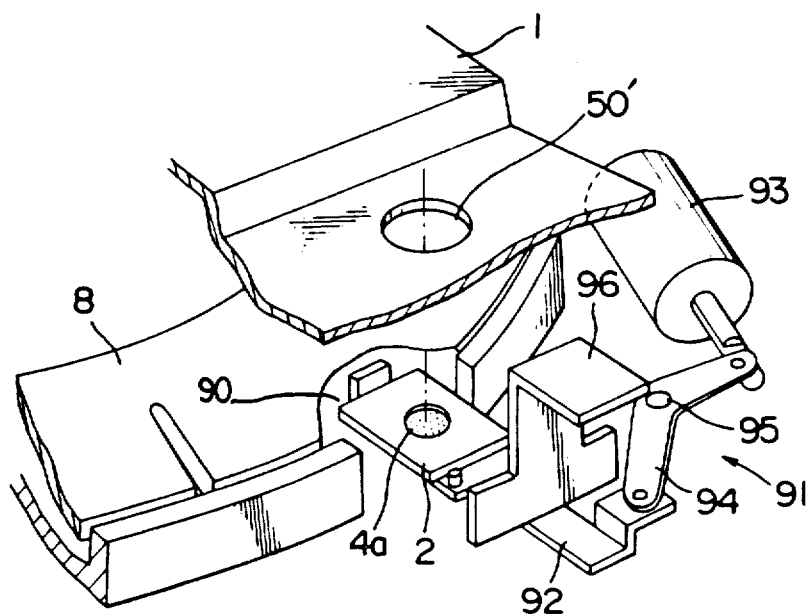

What is claimed is:

1. An apparatus for biochemical analysis comprising:
   conveying means having a plurality of holding portions for holding a plurality of measuring elements, each of said measuring elements including a film impregnated with a reagent;
   driving means for driving said conveying means;
   an insertion unit for inserting each of the plurality of measuring elements into corresponding ones of said holding portions of said conveying means;
   detecting means for detecting the insertion of each of the plurality of measuring elements;
   first control means for controlling the driving means, wherein when the detecting means detects the insertion of one of the plurality of measuring elements, the first control means controls the driving means to rotate the conveying means, thereby enabling the insertion of a subsequent one of the plurality of measuring elements;
   a sample dispensing portion provided in a sample dispensing unit within a main body of said conveying means for dispensing a sample to be measured on said film in desired ones of said measuring elements;
   photometric means for performing a photometric analysis for determining the rate of reaction of the sample with the reagent on the film and desired ones of said measuring elements and for determining the result of a reaction of the sample with the reagent of the film in desired ones of said measuring elements while said plurality of measuring elements are held on said conveying means;
   discharging means for discharging said plurality of measuring elements from said conveying means after the photometric analysis by said photometric means is completed; and
   second control means for sequentially controlling the insertion of said measuring elements, the operation of the sample dispensing unit, the photometric operation and the discharging operation of said measuring elements.

2. An apparatus for biochemical analysis as claimed in claim 1 wherein said photometric means includes:
   photometric calibration means having a first reference plate of a known low optical density and a second reference plate of a known high optical density;
   slide means to constrain said first reference plate and said second reference plate;
   means for operating said slide means for slidingly engaging said conveying means;
   means to slide said slide plate into said conveying means to a first position where said first reference plate is photometrically analyzed and a second position where said second reference plate is photometrically analyzed;
   means to compare measured values from the photometric analysis of said first and second reference plate with predetermined reference values; and
   means to adjust the photometric means for resolving a difference between the measured values and the reference values.

3. An apparatus for biochemical analysis as claimed in claim 1, in which said conveying means further comprises:
   a plurality of fitting grooves, in said conveying means, for removably receiving the plurality of measuring elements;
   a plurality of shoes having said plurality of fitting grooves formed therein;
   a generally rectangular external frame defining a circulation path;
   said shoes slidably disposed along said circulation path; and
   pusher means, mounted on said external frame, for moving said shoes along said circulation path.

4. An apparatus for biochemical analysis as claimed in claim 1 which further comprises:
   identification means disposed on each of the plurality of measuring elements;
   an address code associated with each of the holding portions;
   first reading means to read said identification means; and
   second reading means to read said address code.

5. An apparatus for biochemical analysis as claimed in claim 1 which further comprises:
   a plurality of fitting grooves, in said conveying means, for removably receiving the plurality of measuring elements;
   said conveying means having a top face and a bottom face;
   each of said fitting grooves being in said bottom face and having a radial and circumferential extend sufficient to slidably receive one of the measuring elements;
   at least one identification window extending through said top face of the conveying means to said fitting groove for exposing said first reading means; and
   a sample dispensing window extending form said top face to said fitting groove to provide access to the reagent impregnated film disposed in the measuring element when one of the measuring elements is inserted into said fitting groove.

6. An apparatus for biochemical analysis as claimed in claim 5 wherein each of said fitting grooves has associated therewith an elongated hole extending through said top face to communicate with said fitting groove and extends radially inwardly from said sample dispensing window to at least the inward radial extent of said fitting groove, and wherein said discharging means further includes:
   roller means mounted in said discharging means and located adjacent to said conveying means;
   a discharging pawl operable to enter into said elongated hole and engage the radially inwardmost end of the measuring element and thereby force the measuring element radially outward form said fitting groove into engagement with said roller means; and
   said roller means being operable to engage the measuring element for moving it radially outward from said fitting groove.

7. An apparatus for biochemical analysis as claimed in claim 1 which further comprises:
   rotation means to rotate said conveying means stepwise, each step of said conveying means being equal to the distance between successive ones of said fitting grooves; and
   stop means to hold said conveying means in fixed spaced relation to said main body when said rotation means is not rotating said conveying means.

8. An apparatus for biochemical analysis as claimed in claim 1 wherein said insertion unit comprises:
   an insertion port; and
   roller means operable to engage a measuring element and move it radially inward form said insertion port into said conveying means.

9. An apparatus for biochemical analysis as claimed in claim 1, further comprising:
   timing means for timing a predetermined time interval between the dispensing of the sample to a first measuring element and the photometric operation for the first element; and
   inhibiting means for inhibiting the dispensing of subsequent samples to subsequent measuring elements until the lapse of the predetermined time interval.

10. An apparatus for biochemical analysis as claimed in claim 1, further including:
    item codes disposed on each of said measuring elements for identifying each of said measuring elements;
    address codes associated with each of said holding portions to identify each of said holding portions;
    first reading means for reading said item codes disposed on each of said measuring elements and generating an item signal corresponding thereto;
    second reading means for reading said address codes addresses with each of said holding portions and generating an address signal corresponding thereto;
    memory and correlation means for storing said item and address signals and correlating said address signal to the item signal corresponding to the measuring element disposed in the holding portion;
    first timing means for timing a predetermined time interval as defined by its item code between the dispensing of the sample to a first measuring element and the photometric operation for the first element; and
    inhibiting means for inhibiting the dispensing of subsequent samples to subsequent measuring elements until the lapse of the first predetermined time interval; and
    second timing means for timing a second predetermined time interval as defined by respective item codes between the dispensing of the sample to each measuring element and the photometric operation of each measuring element, wherein said control means controls said driving means at the lapse of the second predetermined time interval so that a corresponding measuring element is brought into operative alignment with said photometric means.

11. An apparatus for biochemical analysis as claimed in claim 1, further including:
    item codes disposed on each of said measuring elements for identifying each of said measuring elements;
    address codes associated with each of said holding portions;
    first reading means for reading said item codes disposed on each of said measuring elements and generating an item signal corresponding thereto;
    second reading means for reading said address codes associated with each of said holding portions and generating an address signal corresponding thereto; and
    memory and correlation means for storing said item and address signals and correlating said address signals to the item signals corresponding to said measuring elements disposed in corresponding ones of said holding portions.

12. An apparatus for biochemical analysis as claimed in claim 1, wherein said conveying means is a disk driven intermittently at predetermined intervals by said driving means, and said insertion unit, sample dispensing portion, photometric means and discharging means are disposed at positions adjacent said conveying means.

13. An apparatus for biochemical analysis as claimed in claim 1, wherein said conveying means is a disk having grooves for holding said measuring elements on a circumferential portion thereof.

14. An apparatus for biochemical analysis as claimed in claim 1, wherein said conveying means is a disk having grooves for holding said measuring elements on a circumferential portion thereof, and further including a thermostatic board including therein a liquid to be heated by heating means disposed adjacent said disk, said measuring element being held in said grooves so that said measuring elements are in contact with said thermostatic board when said disk is rotated.

15. An apparatus for biochemical analysis as claimed in claim 1, further comprising shutter means for closing and opening said sample dispensing unit.

16. An apparatus for biochemical analysis as in claim 15, wherein said shutter means includes means for taking out temporarily said measuring element form said conveying means.

17. An apparatus for biochemical analysis comprising:
    a power switch;
    an endless conveying means having a plurality of holding portions for holding a plurality of measuring elements, each of said measuring elements including a film impregnated with a reagent;
    driving means for driving said conveying means;
    an insertion unit for inserting the measuring elements into said holding portions of said conveying means;

detecting means for detecting the insertion of said measuring elements;

heating means for heating the measuring elements held on said conveying means while said conveying means is driven;

a sample dispensing portion provided in a sample dispensing unit within a main body of said conveying means for dispensing a sample to be measured on said film in desired ones of said measuring elements;

photometric means for performing a photometric analysis for determining the rate of reaction of the sample with the reagent on the film in desired ones of the measuring elements and for determining the result of reaction of the sample with the reagent on the film in desired ones of said measuring elements while said measuring elements are held on said conveying means; and discharging means for discharging the plurality of measuring elements from said conveying means before the photometric analysis by said photometric means begins, said discharging means including control means operable such that when said power switch is turned ON, said conveying means is rotated one rotation, and when a measuring element from a previous photometric analysis is detected on said conveying means by said detecting means, said detected measuring element is discharged by said discharging means; and for discharging said plurality of measuring elements from said conveying means after the photometric analysis by said photometric means is completed.

* * * * *

UNITED STATES PATENT AND TRADEMARK OFFICE
CERTIFICATE OF CORRECTION

PATENT NO. : 5,049,359

DATED : September 17, 1991

INVENTOR(S) : Masahi Azuma et al.

It is certified that error appears in the above-identified patent and that said Letters Patent is hereby corrected as shown below:

Title Page: Inventors, change -- Masahi Azuma--.
to --Masashi Azuma--.

Claim 5, column 16, line 51, change "claim 1" to --claim 4--.

Claim 5, column 16, line 58, change "extend" to --extent--.

Claim 5, column 16, line 64, change "form" to --from--.

Claim 6, column 17, line 14, change "form" to --from--.

Claim 8, column 17, line 33, change "form" to --from--.

Claim 10, column 17, line 55, change "addresses" to --addressed--.

Claim 14, column 18, line 49, change "element" to --elements--.

Claim 16, column 18, line 57, change "form" to --from--.

FIG. 5, change "Dropping" to --Dispensing--.

UNITED STATES PATENT AND TRADEMARK OFFICE
CERTIFICATE OF CORRECTION

Figure 14:
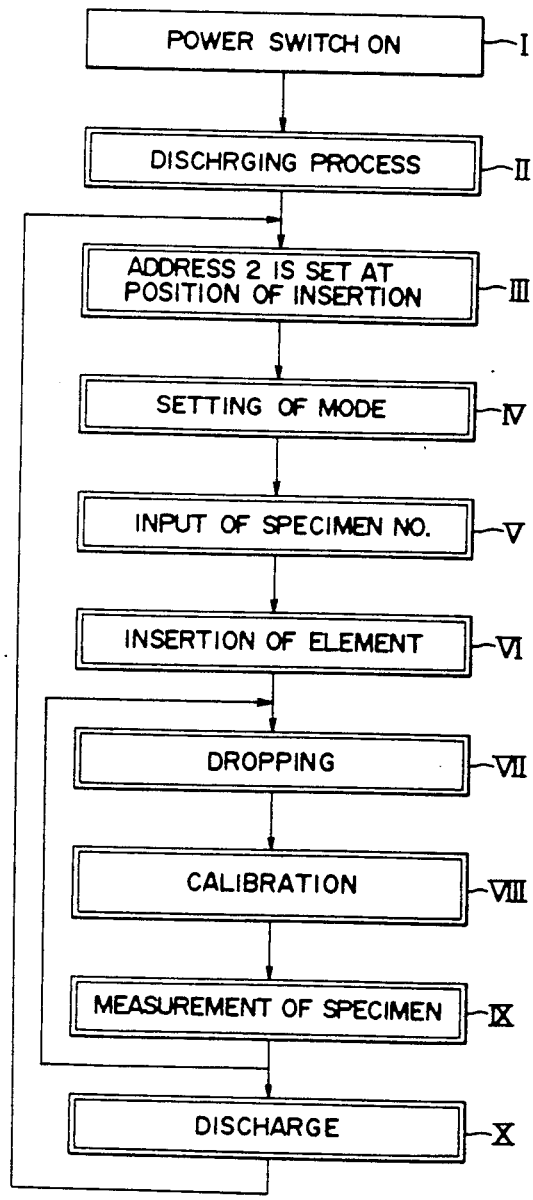
FIG. 14 is a block diagram showing the sequence of operations of the present apparatus.

PATENT NO. : 5,049,359
DATED : September 17, 1991
INVENTOR(S) : Masashi Azuma, et al It is certified that error appears in the above-identified patent and that said Letters Patent is hereby corrected as shown below:

FIG. 14, change "DISCHGING" to --DISCHARGING--.

FIG. 15, change "DROP" to --DISPENSE--.

FIG. 16, change "DROP" to --DISPENSE--.

FIG. 17, change "DROP" to --DISPENSE-- and "DROPPING" to --DISPENSE--.

Figure 21A:
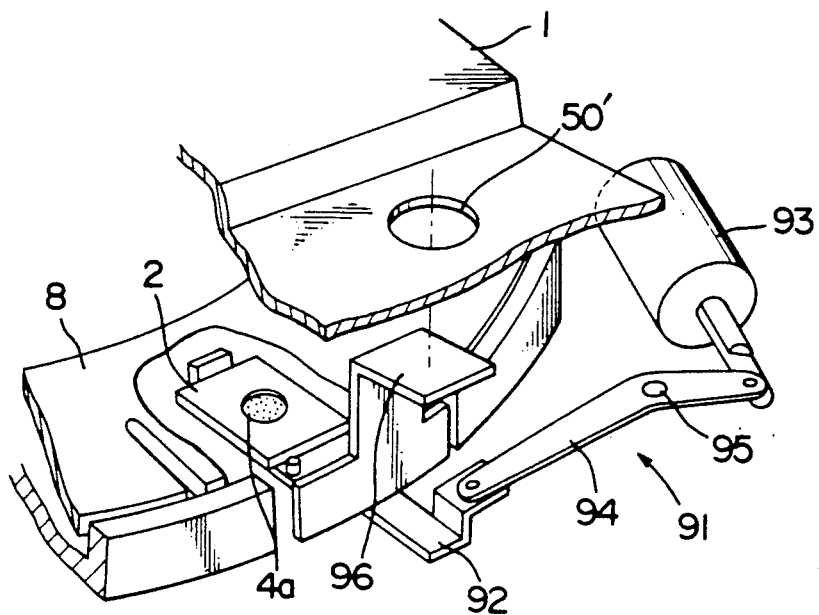
FIGS. 21 A and 21 B are perspective views showing the state of operations of an element reciprocating means thereof.
Figure 21B:
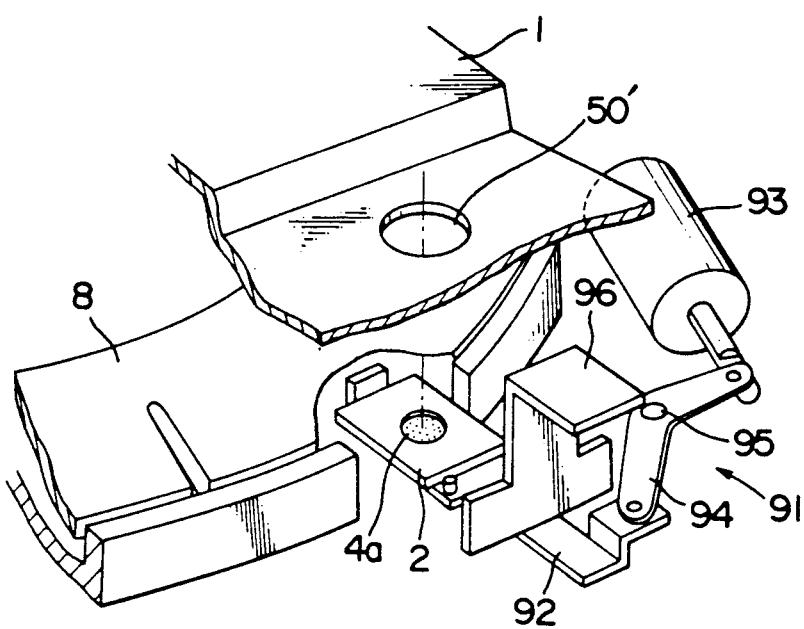
Figure 18A:
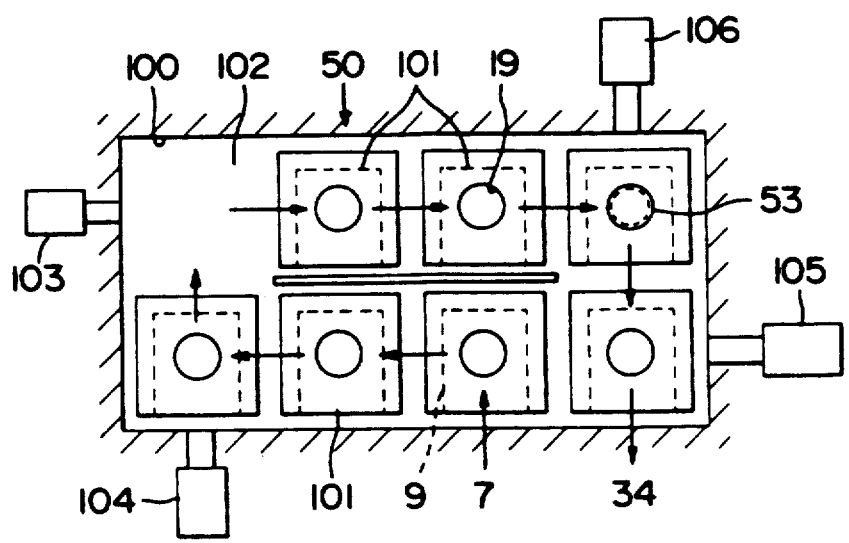
FIGS. 18 A and 18 B are schematic plan views of other examples of a circulation-type conveying means for the measuring elements.
Figure 18B:
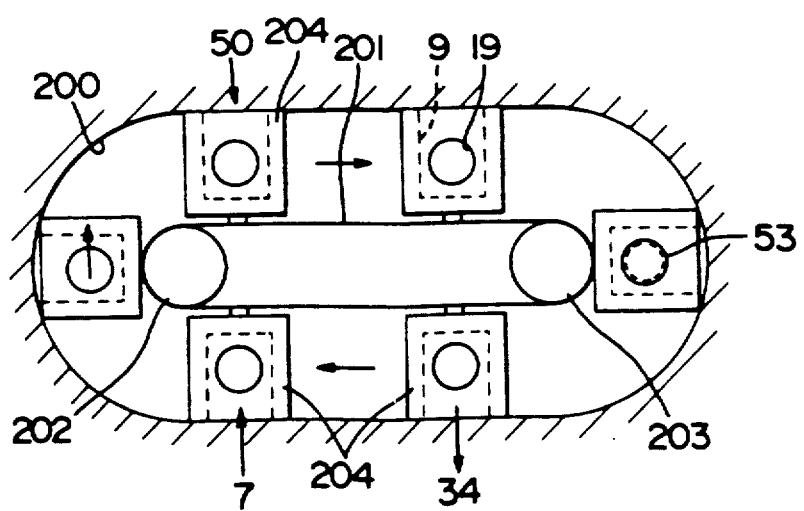

Drawing Sheet 7 of 9, showing FIGS. 21A and 21B, should be deleted and substitute therefor the attached Drawing Sheet 7 of 9, showing FIGS. 18A and 18B.

Drawing Sheet 9 of 9, showing FIGS. 18A and 18B, should be deleted and substitute therefor the attached Drawing Sheet 9 of 9, showing FIGS. 21A and 21B corrected to include reference number --90--.

Signed and Sealed this

Eleventh Day of May, 1993

Attest:

MICHAEL K. KIRK

Attesting Officer    Acting Commissioner of Patents and Trademarks